US012778958B2

(12) United States Patent
Morris et al.

(10) Patent No.: US 12,778,958 B2
(45) Date of Patent: Nov. 3, 2026

(54) MANAGING THE ACUTE AND LONG-TERM EFFECTS OF CORONAVIRAL INFECTIONS AND COMPOSITIONS RELATED THERETO

(71) Applicants: Emory University, Atlanta, GA (US); Children's Healthcare of Atlanta, Inc., Atlanta, GA (US)

(72) Inventors: Claudia R. Morris, Atlanta, GA (US); Lou Ann S. Brown, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 496 days.

(21) Appl. No.: 18/284,236

(22) PCT Filed: Mar. 25, 2022

(86) PCT No.: PCT/US2022/021951
§ 371 (c)(1),
(2) Date: Sep. 26, 2023

(87) PCT Pub. No.: WO2022/204517
PCT Pub. Date: Sep. 29, 2022

(65) Prior Publication Data

US 2024/0115573 A1 Apr. 11, 2024

Related U.S. Application Data

(60) Provisional application No. 63/166,454, filed on Mar. 26, 2021.

(51) Int. Cl.
*A61K 31/198* (2006.01)
*A61K 31/4985* (2006.01)
*A61K 31/519* (2006.01)
*A61K 45/06* (2006.01)

(52) U.S. Cl.
CPC .......... *A61K 31/519* (2013.01); *A61K 31/198* (2013.01); *A61K 45/06* (2013.01)

(58) Field of Classification Search
CPC .............. A61K 31/198; A61K 31/4985; A61K 31/519; A61P 11/00; A61P 9/00; A61P 43/00; A61P 31/14
USPC .................................................. 514/561, 249
See application file for complete search history.

(56) References Cited

U.S. PATENT DOCUMENTS

| | | | | |
|---|---|---|---|---|
| 7,504,384 | B2 | 3/2009 | Yedgar | |
| 10,119,967 | B2 | 11/2018 | Manuguerra | |
| 2006/0105952 | A1 | 5/2006 | Allison | |
| 2009/0018091 | A1 | 1/2009 | Ellis | |
| 2009/0076014 | A1 | 3/2009 | Oppenheimer | |
| 2009/0131342 | A1 | 5/2009 | Ellis | |
| 2013/0116215 | A1* | 5/2013 | Coma .................. | A61K 31/655 514/357 |
| 2016/0199337 | A1 | 7/2016 | Morris | |
| 2019/0307856 | A1 | 10/2019 | Geiger | |

FOREIGN PATENT DOCUMENTS

| | | |
|---|---|---|
| WO | 2003090682 | 11/2003 |
| WO | 2005003164 | 1/2005 |
| WO | 2007086884 | 8/2007 |
| WO | 2015048339 | 4/2015 |

OTHER PUBLICATIONS

Martins, Y.C. et al.: Efficacy of different nitric oxide-based strategies in preventing experimental malaria by plasmodium berghei Anka. PLoS one, vol. 7, e 32048, pp. 1-10, 2012.*
Tratsiakovich, Y. et al. Myocardial protection by co-administration of L-arginine and tetrahydrobiopterin during ischemia and reperfusion. Intern. Journal of Cardiology, vol. 169, pp. 83-88, 2013.*
Kovamees, O. et al.: Effect of argi9nase inhibition on ischemia-reperfusion injury in patients with coronary artery disease with and without diabetes mellitus. PLoS one, vol. 9, e 103260, pp. 1-7, 2014.*
Brothers et al. Racial disparities in cardiovascular disease risk: mechanisms of vascular dysfunction, Am J Physiol Heart Circ Physiol. 2019, 317(4): H777-H789.
Diorio et al. Evidence of thrombotic microangiopathy in children with SARS-CoV-2 across the spectrum of clinical presentations, Blood Adv. 2020, 4(23):6051-6063.
Gambardella et al. Arginine and Endothelial Function, Biomedicines, 2020, 8, 277.
Great Planes Laboratory, Phospholipase A2 (PLA2) And Viruses—How Lowering PLA2 May Help Stifle The Impact Of Serious Viral Infections Like Coronavirus, Restoration Massage and Wellness, available at https://www.facebook.com/permalink.php?story_fbid=4120723461371, 2022.
Grimes et al. Arginine depletion as a therapeutic approach for patients with COVID-19, International Journal of Infectious Diseases 102 (2021) 566-570.
Kidde et al. A Possible Explanation for the COVID-19 Racial Disparity, available at https://www.medpagetoday.com/infectiousdisease/covid19/86023, 2020.
Kokotou et al. Inhibitors of phospholipase A2 and their therapeutic potential: an update on patents, Expert Opinion on Therapeutic Patents, 2017, 27:2, 217-225.
Morris et al. Acquired Amino Acid Deficiencies: A Focus on Arginine and Glutamine, Nutrition in Clinical Practice vol. 32 Supplement, 2017 30S-47S.

(Continued)

*Primary Examiner* — Charanjit Aulakh
(74) *Attorney, Agent, or Firm* — Emory Patent Group

(57) ABSTRACT

This disclosure relates to formulations containing arginine and other ingredients useful in managing acute and chronic complications of coronavirus infections, including respiratory symptoms fatigue, hypercoagulable state, cardiac symptoms, conditions that result from endothelial dysfunction, altered T-cell function/immune dysregulation, mitochondrial dysfunction, and/or and other complications often associated with coronavirus or other viral infections.

19 Claims, 3 Drawing Sheets

(56) References Cited

OTHER PUBLICATIONS

Mouchlis et al., Design of new secreted phospholipase A2 inhibitors based on docking calculations by modifying the pharmacophore segments of the FPL67047XX inhibitor, J Comput Aided Mol Des (2010) 24:107-115.
Muller et al., Inhibition of Cytosolic Phospholipase A2 [alpha] Impairs an Early Step of Coronavirus Replication in Cell Culture, Virol, 2017, 92:e01463-17.
Ong et al. Effects of Antimalarial Drugs on Neuroinflammation-Potential Use for Treatment of COVID-19-Related Neurologic Complications, Molecular Neurobiology (2021) 58:106-117.
Ortea et al. Re-analysis of SARS-CoV-2 infected host cell proteomics time-course data by impact pathway analysis and network analysis. A potential link with inflammatory response, bioRxiv 2020, available at doi: https://doi.org/10.1101/2020.03.26.009605.
Oslund et al. Highly Specific and Broadly Potent Inhibitors of Mammalian Secreted Phospholipases A2, J. Med. Chem. 2008, 51, 4708-4714.
Oslund et al. Inhibition of secreted phospholipases A2 by 2-oxoamides based on [alpha]-amino acids: Synthesis, in vitro evaluation and molecular docking calculations, Bioorg Med Chem. 2011, 19(2): 735-743.
Pungercar et al. What do secreted phospholipases A2 have to offer in combat against different viruses up to SARS-CoV-2? Biochimie 189 (2021) 40-50.
Rees et al. Altered amino acid profile in patients with SARS-CoV-2 infection, PNAS 2021 vol. 118 No. 25 e2101708118.
Reizine et al. SARS-CoV-2-Induced ARDS Associates with MDSC Expansion, Lymphocyte Dysfunction, and Arginine Shortage, J Clin Immunol. 2021, 41(3):515-525.
Vasilakaki et al. Development of a potent 2-oxoamide inhibitor of secreted phospholipase A2 guided by molecular docking calculations and molecular dynamics simulations, Bioorg Med Chem. 2016, 24(8): 1683-1695.
Vijay et al. Critical role of phospholipase A2 group IID in age-related susceptibility to severe acute respiratory syndrome—CoV infection, J. Exp. Med. 2015 vol. 212 No. 11 1851-1868.

* cited by examiner

| Clinical Characteristics | Controls (n=28) | Adult COVID-19 (n=32) | Pediatric COVID-19/MIS-C (n=20) |
|---|---|---|---|
| *Patient Demographics* | | | |
| Mean Age±SD (Range in years) | (41-50)*** | 60±17 (20-99) | 11±5 (3-20) |
| Female, n (%) | 20 (71.4) | 11 (34.3) | 10 (50.0) |
| Comorbidity present, n (%) | 4 (14.3) | 17 (53.1) | 5 (25.0) |
| Multisystem inflammatory syndrome in children, n (%) | - | - | 9 (45.0) |
| Infiltrate on chest x-ray, n (%) | - | 28 (87.5) | 15 (75.0) |
| Supplemental oxygen, n (%) | - | 19 (59.4) | 14 (70.0) |
| Ventilator use, n (%) | - | 7 (21.9) | 3 (15.0) |
| Intensive care unit, n (%) | - | 9 (28.1) | 16 (80.0) |
| Total days in hospital, Median (IQR) | - | 18.25 (14-31) | 9 (8-22) |
| Death, n (%) | - | 3 (9.4) | 2 (10.0) |

FIG. 4

| Amino acids (μmol/L) | Controls | Adult COVID-19 | Pediatric COVID-19/MIS-C |
|---|---|---|---|
| ***Arginine Pathway Related Amino Acids and Ratios*** | | | |
| Arginine | 92.9 (29.2) | 58.2 (50.8) | 52.0 (52.3) |
| Ornithine | 98.5 (30.1) | 110.0 (51.3) | 110.7 (65.7) |
| Citrulline | 18.4 (4.1) | 12.8 (6.9) | 6.9 (5.1) |
| Glutamate | 211.4 (63.7) | 213.9 (132.4) | 165.1 (123.3) |
| Glutamine | 1,023.0 (163.7) | 614.5 (282.2) | 910.6 (293.5) |
| Arginine-to-Ornithine Ratio | 1.01 (0.40) | 0.55 (0.46) | 0.52 (0.45) |
| Global Arginine Bioavailability Ratio | 0.84 (0.31) | 0.48 (0.38) | 0.49 (0.43) |
| Glutamine-to-Glutamate Ratio | 5.41 (2.24) | 4.69 (3.73) | 8.62 (5.92) |
| ***Other Amino Acids*** | | | |
| Alanine | 504.7 (98.0) | 328.9 (114.6) | 331.0 (119.1) |
| Cysteine | 4.3 (1.5) | 4.0 (1.4) | 4.1 (2.0) |
| Cystine | 7.0 (3.5) | 7.2 (5.7) | 11.7 (6.6) |
| Glycine | 6,684.0 (2,197) | 4,286.2 (1,195) | 5,606.1 (1,505) |
| Histidine | 76.2 (14.3) | 39.3 (23.5) | 52.9 (27.0) |
| Isoleucine | 20.2 (5.4) | 18.7 (7.4) | 16.0 (8.4) |
| Leucine | 106.8 (39.2) | 102.1 (63.8) | 77.3 (65.5) |
| Lysine | 231.2 (37.5) | 219.0 (68.3) | 202.5 (99.4) |
| Methionine | 25.4 (7.0) | 21.2 (7.9) | 21.9 (12.6) |
| Phenylalanine | 40.8 (7.1) | 57.7 (42.7) | 55.4 (23.4) |
| Proline | 246.4 (63.4) | 176.3 (65.3) | 175.2 (79.4) |
| Serine | 267.1 (58.5) | 212.7 (74.6) | 298.0 (111.8) |
| Threonine | 40.6 (11.3) | 34.7 (13.5) | 42.0 (25.1) |
| Tryptophan | 40.8 (7.3) | 21.6 (7.0) | 20.5 (10.7) |
| Tyrosine | 46.2 (10.1) | 65.4 (38.1) | 32.7 (11.7) |
| Valine | 190.7 (41.2) | 214.6 (82.5) | 167.2 (66.3) |

FIG. 5

MANAGING THE ACUTE AND LONG-TERM EFFECTS OF CORONAVIRAL INFECTIONS AND COMPOSITIONS RELATED THERETO

CROSS-REFERENCE TO RELATED APPLICATIONS

This application is the National Stage of International Application No. PCT/US2022/021951 filed Mar. 25, 2022, which claims the benefit of U.S. Provisional Application No. 63/166,454 filed Mar. 26, 2021. The entirety of each of these applications is hereby incorporated by reference for all purposes.

BACKGROUND

Some common colds are due to certain coronavirus (CoV) strains associated with mild symptoms. More dangerous human strains such as severe acute respiratory syndrome associated coronavirus (SARS-CoV-1) and SARS-CoV-2 (also referred to as COVID-19) are believed to result from coronavirus strains jumping to humans by secondary zoonotic transfers, e.g., from bats to cats and cats to humans. In humans, SARS-CoV-2 can be transferred from individuals who have mild symptoms or are asymptomatic and has caused numerous deaths worldwide. COVID-19 patients that have recovered are over time reporting persistent, new, or worsening symptoms such as shortness of breath, fatigue, joint pain, and chest pain. Many patients report experiencing multiple symptoms for several months after symptom onset. Thus, there is a need to find effective methods of managing these post-infection complications.

Morris, et al. report low arginine bioavailability plays a role in the pathogenesis of varied diseases. Nutr Clin Pract. 32, 30S-47S (2017).

Diorio et al. report evidence of thrombotic microangiopathy in children with Sars-Cov-2 across the spectrum of clinical presentations. Blood Adv. 136, 28-29 (2020).

Gambardella et al. report a role of arginine in the regulation of endothelial function and vascular tone. Biomedicines. 8, 277 (2020).

Grimes et al. report arginine depletion as a therapeutic approach for patients with COVID-19. Int J Infect Dis. 102, 566-570 (2020).

Reizine et al. report SARS-CoV-2-induced ARDS associates with MDSC expansion, lymphocyte dysfunction, and arginine shortage. J Clin Immunol. 2021, 41(3):515-525

References cited herein are not an admission of prior art.

SUMMARY

This disclosure relates to formulations containing arginine and other ingredients useful in managing acute and chronic complications of coronavirus infections, including respiratory symptoms fatigue, hypercoagulable state, cardiac symptoms, conditions that result from endothelial dysfunction, altered T-cell function/immune dysregulation, mitochondrial dysfunction, and/or and other complications often associated with coronavirus or other viral infections.

In certain embodiments, this disclosure relates to improving cardiac, neuropsychic, immune function, hypercoagulation, and/or mitochondrial dysfunction due to a coronavirus or other viral infections comprising administering a composition comprising an effective amount of arginine and other ingredients to a subject in need thereof.

In certain embodiments, this disclosure relates to treating or preventing chronic acute respiratory syndrome or associated side effects due to a coronavirus or other viral infections comprising administering a composition comprising an effective amount of arginine and other ingredients to a subject in need thereof.

In certain embodiments, the formulations are administered daily, up to 2 times a day, 3 times a day, or as a continuous infusion. In certain embodiments, contemplates is a boost drink for consuming several times a day e.g., two or three or up to 3 times a day, or as a continuous enteral feeding (NG) for severely ill and/or hospitalized subjects.

In certain embodiments, this disclosure relates to treating or preventing chronic acute respiratory syndrome or associated side effects comprising administering a composition comprising an effective amount of arginine, a biopterin such as tetrahydrobiopterin, and optionally an arginase inhibitor to a subject in need thereof. In certain embodiments, the biopterin is biopterin, dihydrobiopterin, tetrahydrobiopterin, or combinations thereof.

In certain embodiments, the subject is diagnosed with a viral infection that poses a risk of developing an acute respiratory syndrome or chronic acute respiratory syndrome such as subject diagnosed with a coronavirus infection, e.g., SARS-CoV-1 or SARS-CoV-2 infection.

In certain embodiments, the subject is diagnosed with multisystem inflammatory syndrome (MIS) and/or post-COVID long hauler complications, in children (MIS-C) and in adults (MIS-A).

In certain embodiments, the formula is a composition administered daily. In certain embodiments, the composition is administered daily for more than 3, 5, 7 days or two weeks. In certain embodiments, the composition is administered daily for more than one month or two months.

In certain embodiments, the formula comprises arginine for administration of up to 10 grams per dose or up to 30 grams per day.

In certain embodiments, the formula dose can be adjusted by weight for children or adults for an arginine component dose of 100 mg/kg-300 mg/kg per dose, typically 100-200 mg/kg for children.

In certain embodiments, the subject is any age, e.g., less than 25, 20, 15, or 10 years old or the subject is more than 55, 65, or 75 years old.

In certain embodiments, the subject is diagnosed with fatigue, shortness of breath, anxiety, depression, brain fog, joint pain, and/or chest pain, and optionally diabetes, stroke, heart rhythm abnormality, and/or blood clot in the lungs.

In certain embodiments, the subject is more than 55, 65, or 75 years old and/or diagnosed with a severe acute infection requiring intensive care, pre-existing respiratory illness, obesity, diabetes, high blood pressure, chronic cardiovascular disease, chronic kidney disease, organ transplant, or cancer.

In certain embodiments, this disclosure relates to compositions comprising arginine, a biopterin such as tetrahydrobiopterin, and optionally an arginase inhibitor. In certain embodiments, the composition further comprises glutamine. In certain embodiments, the composition further comprises 5-hydroxytryptophan. In certain embodiments, the composition further comprises citrulline. In certain embodiments, the composition further comprises glycine.

In certain embodiments, this disclosure relates to compositions comprising arginine, a biopterin such as tetrahydrobiopterin, glutamine, tryptophan, 5-hydroxytryptophan, citrulline, and optionally an arginase inhibitor.

In certain embodiments, any of the formulations disclosed herein further comprise additional amino acids especially the essential amino acids.

In certain embodiments, this disclosure contemplates an enteral formula comprising ingredients of a medical meal replacement formula with additional vitamins and minerals.

In certain embodiments, this disclosure contemplates enteral formula for treating a subject diagnosed with COVID-19. In certain embodiments, the subject is placed on enteral formulas or parenteral nutrition providing a balance of fats, proteins, sugars, vitamins, and minerals.

In certain embodiments, the formula is delivered into the gut to be absorbed.

In certain embodiments, the formula is delivered into the blood stream through a drip to bypass the gut, i.e., tube-fed.

In certain embodiments, this disclosure contemplates an intravenous formulation with pH buffering agents and tonicity in a range representing physiological values (pH 7 to 8) or for bolus administration, e.g., containing normal saline or dextrose optionally containing pH buffering agents.

In certain embodiments, the formula further comprises zinc, vitamin D, multiple vitamins, arginine, tetrahydrobiopterin, and 5-hydroxytryptophan.

In certain embodiments, this disclosure contemplates a formulation supplement that a less sick person may take 1-3 times per day, e.g., as a drink or in pill form.

BRIEF DESCRIPTION OF THE SEVERAL VIEWS OF THE DRAWINGS

FIG. 4 shows a table of demographics controls compared to adult and pediatric COVID-19 patients.

FIG. 5 shows a table of distribution of plasma amino acid levels in controls compared to adult and pediatric COVID-19 patients.

DETAILED DISCUSSION

Figure 1:
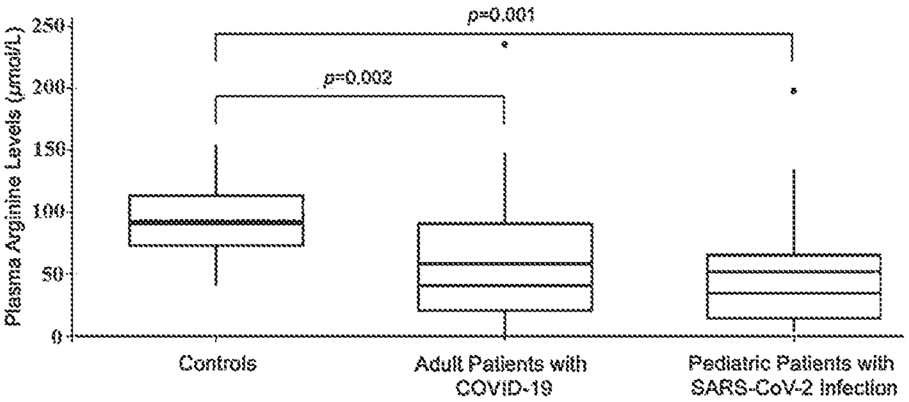
FIG. 1 shows data on plasma arginine bioavailability among the three cohorts.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Prior to describing the various embodiments, the following definitions are provided and should be used unless otherwise indicated.

It must be noted that, as used in the specification and the appended claims, the singular forms "a," "an," and "the" include plural referents unless the context clearly dictates otherwise. Thus, for example, reference to "an omega-3 fatty acid" includes a plurality of such fatty acids and reference to "the vitamin E" includes reference to one or more vitamin E isoforms and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As used herein, "subject" refers to any animal, typically a human patient, livestock, or domestic pet such as a dog.

As used herein, the terms "prevent" and "preventing" include the prevention of the recurrence, spread or onset. It is not intended that the present disclosure be limited to complete prevention. In some embodiments, the onset is delayed, or the severity of the disease or condition is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Arginase is an enzyme containing manganese that converts L-arginine into L-ornithine and urea. An "arginase inhibitor" is a compound that specifically binds with an arginase preventing or slowing the conversion of L-arginine. There are two arginase isoforms, arginase 1 and 2, which are encoded by different genes and differentially expressed in the body. Arginase 1 is a cytosolic enzyme which is primarily located in the liver, though it is also expressed in extra-hepatic tissues.

A "biopterin" refers to family of molecules containing a pterin core structure, i.e., 2-aminopteridin-4(3H)-one, derivatives, tautomers or reduced forms thereof, such as biopterin with the chemical name 2-amino-6-(1,2-dihydroxypropyl)-1H-pteridin-4-one; sepiapterin with the chemical name 2-amino-6-[2-hydroxypropanoyl]-7,8-dihydro-1H-pteridin-4-one; and tetrahydrobiopterin with the chemical name 5,6,7,8-Tetrahydro-2-amino-6-(1,2-dihydroxypropyl)-4(1H)-pteridinone (THB). Other contemplated examples include molybdopterin and folate.

"Fatty acids" refers to a family of carboxylic acids having a saturated or unsaturated hydrocarbon chain of about 4 to about 28 carbons in length and is intended to include carboxylic acid salt forms. Medium chain fatty acids (MCFAs) refer to a family of carboxylic acids having a saturated or unsaturated hydrocarbon chain of from about 6 to 10 carbons in length and is intended to include carboxylic acid salt forms. Examples include capric acid, caprylic acid, and hexanoic acid. Medium-chain triglycerides (MCTs) are esters (tri-, di-, monoglyceride esters) of medium chain fatty acids and glycerol. Natural sources of MCFAs and MCTs include coconut, palm kernel oil, and bovine milk. One method of producing MCT is by hydrolysis of coconut or palm kernel oil, filtration of MCFAs, and subsequent re-esterification of the MCFAs with glycerol. Oils produced by re-esterification contain mostly caprylic acid (octanoic) and capric acid (decanoic acid), at a ratio from about 50:50 to 80:20 with typically less than 5% of long chain or shorter chain acids. Long chain fatty acids are typically between 12 and 28 carbons in length. Unsaturated fatty acids have at least one carbon-carbon double bond in the hydrocarbon chain. Unsaturated fatty acids include monounsaturated fatty acids and polyunsaturated fatty acids (PUFAs). Unsaturated fatty acids are designated by the position of the first double bond from the methyl end of the hydrocarbon chain.

Omega-3 fatty acids have a first double bond at the third carbon from the methyl end of the chain; and include, e.g., alpha-linolenic acid (octadeca-9,12,15-trienoic acid), stearidonic acid (octadeca-6,9,12,15-tetraenoic acid), eicosapentaenoic acid (eicosa-5,8,11,14,17-pentaenoic acid; "EPA"), docosapentaenoic acid (docosa-7,10,13,16,19-pentaenoic acid), eicosatetraenoic acid (eicosa-8,11,14,17-tetraenoic acid), and docosahexaenoic acid (docosa-4,7,10,13,16,19-hexaenoic acid; "DHA"). Ethyl eicosapentaenoate, icosapent ethyl (Vascepa™) is an omega-3 polyunsaturated fatty acid (PUFA) ester composition FDA approved for the treatment of hypertriglyceridemia.

Omega-6 fatty acids have a first double bond at the sixth carbon from the methyl end of the chain; and include, e.g., linoleic acid (9,12-octadecadienoic acid), gamma-linolenic acid (6,9,12-octadecatrienoic acid; GLA), eicosadienoic acid (11,14-eicosadienoic acid), dihomo-gamma-linolenic acid (8,11,14-eicosatrienoic acid), arachidonic acid (5,8,11,14-eicosatetraenoic acid), docosadienoic acid (13,16-docosadienoic acid), adrenic acid (7,10,13,16-docosatetraenoic acid), docosapentaenoic acid (4,7,10,13,16-docosapentaenoic acid), and calendic acid (8E,10E,12Z-octadecatrienoic acid), and the like. Omega-9 fatty acids have a first double bond at the ninth carbon from the methyl end of the chain; and include, e.g., oleic acid (cis-9-octadecenoic acid); eicosenoic acid (cis-11-eicosenoic acid); mead acid (all-cis-5,8,11-eicosatrienoic acid); erucic acid (cis-13-docosenoic acid); and nervonic acid (cis-15-tetracosenoic acid).

As used herein, a "vitamin D" refers to a family of fat-soluble steroids derived from 7-dehydrocholesterol, ergosterol and 7-dehydrositosterol. Examples include cholecalciferol ergocalciferol, lumisterol, sitocalciferol, and 22-dihydroergocalciferol.

As used herein, a "vitamin E" refers to a family of molecules having a chromanol ring (chroman ring with an alcoholic hydroxyl group) and a 12-carbon aliphatic side chain containing two methyl groups in the middle and two more methyl groups at the end. The side chain of the tocopherols is saturated, while the side chain of the tocotrienols contain three double-bonds, all of which adjoin a methyl group. The tocopherols and the tocotrienols exist in four isoforms, referred to as alpha, beta, gamma, and delta isoforms. The isoforms are named on the basis of the number and position of the methyl groups on the chromanol ring. The alpha form has three methyl groups, the beta and gamma forms have two methyl groups and the delta for has only one methyl group. A "vitamin E" may be alpha-tocopherol, beta-tocopherol, gamma-tocopherol, alpha-tocotrienol, beta-tocotrienol, and gamma-tocotrienol. A "vitamin E" also includes esters of a vitamin E isoform. For example, a "vitamin E" includes esters of a tocopherol, including acetates and succinates.

As used herein, the term a "lipoic acid" refers to alpha-lipoic acid, which is a chiral molecule also known as 6,8-dithioloctanoic acid. Unless specified the term "lipoic acid" encompasses the racemic mixture as well as any other (non-50/50) mixture of the enantiomers, such as substantially pure forms of either the R-(+) or the S-(−) enantiomer. Further, unless specified otherwise the term covers salts (e.g. Na and K salts) and amides, esters and metabolites of the acid.

"Carnitine" is also known as 3-hydroxy-4-(trimethylazaniumyl)butanoate. As used herein, the term a "carnitine" includes carnitine and "carnitine analogs" and encompasses racemic or essentially pure L-carnitine (carnitine), or a corresponding alkanoyl-carnitine such as acetyl-carnitine or propionyl-carnitine, or a suitable salt of such compounds such as L-carnitine tartrate, L-carnitine fumarate, L-carnitine-magnesium-citrate, acetyl-L-carnitine tartrate, acetyl-L-carnitine-magnesium-citrate, or any mixture of the aforementioned compounds.

Certain of the compounds described herein may contain one or more asymmetric centers and may give rise to enantiomers, diastereomers, and other stereoisomeric forms that can be defined, in terms of absolute stereochemistry at each asymmetric atom, as (R)- or (S)-. The present chemical entities, compositions and methods are meant to include all such possible isomers, including racemic mixtures, tautomer forms, hydrated forms, optically substantially pure forms, and intermediate mixtures. In certain embodiments, the compounds may be present in a composition with enantiomeric excess or diastereomeric excess of greater than 60%. In certain embodiments, the compounds may be present in enantiomeric excess or diastereomeric excess of greater than 70%. In certain embodiments, the compounds may be present in enantiomeric excess or diastereomeric excess of greater than 80%. In certain embodiments, the compounds may be present in enantiomeric excess or diastereomeric excess of greater than 90%. In certain embodiments, the compounds may be present in enantiomeric excess or diastereomeric excess of greater than 95%.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single for a double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative and an alkyl ester of a carboxylic acid is a contemplated derivative. The derivative may be a prodrug.

Derivatives may be prepared by any variety of synthetic methods or appropriate adaptations presented in the chemical literature or as in synthetic or organic chemistry textbooks, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in compositions over the parent drug. A prodrug may be converted into the parent drug by various mechanisms, including enzymatic processes and metabolic hydrolysis.

Typical prodrugs are esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

As used herein, "esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO2Rb, —C(═O)Ra, —C(═O)ORa, —C(═O)NRaRb, —OC(═O)NRaRb, —ORa, —SRa, —SORa, —S(═O)$_2$Ra, —OS(═O)$_2$Ra and —S(═O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic. "Arylalkyl" means an alkyl substituted with an aryl, e.g., benzyl, methyl substituted with phenyl.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers to an alkyl group as defined above attached through an amino bridge. An example of an alkylamino is methylamino, (i.e., —NH—$CH_3$).

"Alkanoyl" refers to an alkyl as defined above attached through a carbonyl bridge (i.e., —(C=O)alkyl).

Methods of Use

This disclosure relates to formulations containing arginine and other ingredients useful in managing acute and chronic complications of coronavirus infections, including respiratory symptoms fatigue, hypercoagulable state, cardiac symptoms, conditions that result from endothelial dysfunction altered T-cell function/immune dysregulation, and/or and other complications often associated with coronavirus or other viral infections.

In certain embodiments, this disclosure relates to improving cardiac, neuropsychic, immune function, hypercoagulation, or mitochondrial dysfunction due to a coronavirus or other viral infections comprising administering a composition comprising an effective amount of arginine and other ingredients to a subject in need thereof.

In certain embodiments, this disclosure relates to treating or preventing chronic acute respiratory syndrome or associated side effects due to a coronavirus or other viral infections comprising administering a composition comprising an effective amount of arginine and other ingredients to a subject in need thereof.

In certain embodiments, the formulations are administered daily, up to 2 times a day, 3 times a day, or as a continuous infusion. In certain embodiments, contemplates is a boost drink for consuming several times a day e.g., two or three or up to 3 times a day, or as a continuous enteral feeding (NG) for severely ill and/or hospitalized subjects.

In certain embodiments, this disclosure relates to treating or preventing chronic acute respiratory syndrome or associated side effects comprising administering a composition comprising an effective amount of arginine, a biopterin such as tetrahydrobiopterin, and optionally an arginase inhibitor to a subject in need thereof. In certain embodiments, the biopterin is biopterin, dihydrobiopterin, tetrahydrobiopterin, or combinations thereof.

In certain embodiments, it is contemplated that disclosed formulas will treat endothelial dysfunction, immune issues, and hypercoagulation in addition to respiratory symptoms. In certain embodiments, it is contemplated that disclosed formulas will treat neuropsychiatric benefits as tetrahydrobiopterin is use to make nitric oxide, but also to convert tryptophan to 5-hydroxytryptophan which impacts serotonin.

In certain embodiments, the subject is diagnosed with a viral infection that poses a risk of developing an acute respiratory syndrome or chronic acute respiratory syndrome such as subject diagnosed with a coronavirus infection, e.g., SARS-CoV-1 or SARS-CoV-2 infection.

In certain embodiments, the subject is diagnosed with multisystem inflammatory syndrome (MISC) and/or post-COVID long hauler complications.

In certain embodiments, the formula is a composition administered daily. In certain embodiments, the composition is administered daily for more than 3, 5, 7 days or two weeks. In certain embodiments, the composition is administered daily for more than one month or two months.

In certain embodiments, the formula comprises arginine for administration of up to 10 grams per dose or up to 30 grams per day.

In certain embodiments, the formula dose can be adjusted by weight for children or adults for an arginine component dose of 100 mg/kg-300 mg/kg per dose.

In certain embodiments, the subject is any age, e.g., less than 25, 20, 15, or 10 years old or the subject is more than 55, 65, or 75 years old.

In certain embodiments, the subject is diagnosed with fatigue, shortness of breath, anxiety, depression, brain fog, joint pain, and/or chest pain, and optionally diabetes, stroke, heart rhythm abnormality, and/or blood clot in the lungs.

In certain embodiments, the subject is more than 55, 65, or 75 years old and/or diagnosed with a severe acute infection requiring intensive care, pre-existing respiratory illness, obesity, diabetes, high blood pressure, chronic cardiovascular disease, chronic kidney disease, organ transplant, or cancer.

This disclosure relates to nutritional formulations containing arginine and other ingredients useful in managing respiratory dysfunction and other complications often associated with coronavirus or other viral infections. In certain embodiments, this disclosure relates to treating or preventing chronic acute respiratory syndrome or associated side effects comprising administering a composition comprising an effective amount of arginine and other optional ingredients to a subject in need thereof. In certain embodiments, the formulations are administered daily.

In certain embodiments, this disclosure relates to treating or preventing chronic acute respiratory syndrome or associated side effects comprising administering a composition comprising an effective amount of arginine, a biopterin such as tetrahydrobiopterin, and optionally an arginase inhibitor to a subject in need thereof. In certain embodiments, the biopterin is biopterin, dihydrobiopterin, tetrahydrobiopterin, or combinations thereof.

In certain embodiments, the subject is diagnosed with a viral infection that poses a risk of developing an acute respiratory syndrome or chronic acute respiratory syndrome such as subject diagnosed with a coronavirus infection, e.g., SARS-CoV-1 or SARS-CoV-2 infection.

In certain embodiments, the nutritional formula is a composition administered daily. In certain embodiments, the composition is administered daily for more than 3, 5, 7 days or two weeks.

In certain embodiments, the nutritional formula comprises arginine for administration of up to 10 grams per dose or up to 30 grams per day.

In certain embodiments, the subject is diagnosed with multisystem inflammatory syndrome (MISC) and/or post-COVID long hauler complications.

In certain embodiments, the subject is less than 25, 20, 15, or 10 years old.

In certain embodiments, the subject is diagnosed with fatigue, shortness of breath, brain fog, joint pain, and/or chest pain, and optionally diabetes, stroke, heart rhythm abnormality, and/or blood clot in the lungs In certain embodiments, the subject is more than 55, 65, or 75 years old and/or diagnosed with a severe acute infection requiring intensive care, pre-existing respiratory illness, obesity, diabetes, high blood pressure, chronic cardiovascular disease, chronic kidney disease, organ transplant, or cancer.

Formulations

In certain embodiments, this disclosure relates to formulations and compositions comprising arginine, a biopterin such as tetrahydrobiopterin, and optionally an arginase inhibitor for use in managing coronavirus or other viral infections.

In certain embodiments, this disclosure relates to compositions comprising arginine, a biopterin such as tetrahydrobiopterin, glutamine, tryptophan, citrulline, and optionally an arginase inhibitor.

In certain embodiments, the arginase inhibitor is alpha-difluoromethylornithine (DMFO), its derivative, or salts thereof. In certain embodiments, the arginase inhibitor is No-hydroxy-nor-L-arginine (nor-NOHA), its derivative, or salts thereof. In certain embodiments, the arginase inhibitor is sauchinone, its derivative, or salts thereof. In certain embodiments, the arginase inhibitor is salvianolic acid B (SAB), its derivative, or salts thereof. In certain embodiments, the arginase inhibitor is piceatannol-3-O-β-D-glucopyranoside (PG), its derivative, or salts thereof. In certain embodiments, the arginase inhibitor is obacunone, its derivative, or salts thereof. In certain embodiments, arginase inhibitor is L-norvaline, its derivative, or salts thereof. In certain embodiments, the arginase inhibitor is trihydroxy-7,8-dimethoxy-flavanone (TDF), its derivative, or salts thereof. In certain embodiments, the arginase inhibitor is 2-(S)-amino-5-(2-aminoimidazol-1-yl)pentanoic acid, its derivative, or salts thereof. In certain embodiments, the arginase inhibitor is (E)-N-(2-phenylethyl)-3,4-dihydroxycinnamide, its derivative, or salts thereof.

In certain embodiments, the arginase inhibitor is chloroquine, its derivative, or salts thereof. In certain embodiments, the arginase inhibitor is darunavir, its derivative, or salts thereof. In certain embodiments, the arginase inhibitor is atazanavir, its derivative, or salts thereof. In certain embodiments, the arginase inhibitor is efavirenz, its derivative, or salts thereof. In certain embodiments, the arginase inhibitor is nevirapine, its derivative, or salts thereof.

In certain embodiments, the arginase inhibitor is an amino acid derivative that contains a boronic acid side chain, salt, or ester thereof. In certain embodiments, arginase inhibitor is 2(S)-amino-6-boronohexanoic acid, its derivative, or salts thereof. In certain embodiments, the arginase inhibitor is S-(2-boronoethyl)-L-cysteine (BEC), its derivative, or salts thereof. In certain embodiments, arginase inhibitor is 2(S)-amino-6-boronohexanoic acid, its derivative, or salts thereof. In certain embodiments, the arginase inhibitor is S-(2-boronoethyl)-L-cysteine (BEC), its derivative, or salts thereof. In certain embodiments, the arginase inhibitor is 2-amino-6-borono-2-(2-(pyrrolidin-1-yl)ethyl)hexanoic acid, its derivative, or salts thereof. In certain embodiments, the arginase inhibitor is (3R,4S)-1-(L-alanyl)-3-amino-4-(3-(dihydroxy-bromaneyl)propyl) pyrrolidine-3-carboxylic acid, its derivative, or salts thereof (CB-1158). In certain embodiments, the arginase inhibitor is 2-amino-6-borono-2-(6-(4-chlorobenzyl)-6-azabicyclo[3.1.1]heptan-3-yl) hexanoic acid, its derivative, or salts thereof. In certain embodiments, the arginase inhibitor is 2-amino-6-borono-2-(6-(3,4-dichlorobenzyl)-6-azabicyclo[3.1.1]heptan-3-yl) hexanoic acid, its derivative, or salts thereof. In certain embodiments, the arginase inhibitor is 1-alanyl-3-amino-4-(3-boronopropyl)pyrrolidine-3-carboxylic acid, its derivative, or salts thereof. In certain embodiments, the arginase inhibitor is (6aS,9aR)-9a-amino-3-ethoxy-8-glycyloctahydro-[1,2]oxaborocino[6,7-c]pyrrol-1(3H)-one, its derivative, or salts thereof. In certain embodiments, the arginase inhibitor is (6aS,9aR)-8-alanyl-9a-amino-3-ethoxyoctahydro-[1,2]oxaborocino[6,7-c]pyrrol-1(3H)-one, its derivative, or salts thereof. In certain embodiments, the arginase inhibitor is (6aS,9aR)-8-alanyl-9a-amino-3-isopropoxyoctahydro-[1,2]oxaborocino[6,7-c]pyrrol-1(3H)-one its derivative, or salts thereof.

In certain embodiments, the composition further comprises 5-hydroxytryptophan.

In certain embodiments, the composition further comprises sPLA2 inhibitor such as diannexin, annexin V, varespladib, varespladib methyl ester, varespladib ethyl ester, and darapladib.

In certain embodiments, the sPLA2 inhibitor is (S)-4-Methyl-2-(2-oxohexadecanamido)pentanoic acid (GK126) or derivatives. See Mouchlis et al., Inhibition of secreted phospholipases A2 by 2-oxoamides based on α-amino acids: Synthesis, in vitro evaluation and molecular docking calculations, Bioorg Med Chem, 2011, 19(2): 735-743.

In certain embodiments, the sPLA2 inhibitor is S)-3-Methyl 2-(2-oxohexadecanamido)butanoic acid (16a, GK241). See Vasilakaki et al. Development of a potent 2-oxoamide inhibitor of secreted phospholipase A2 guided by molecular docking calculations and molecular dynamics simulations. Bioorg Med Chem, 2016, 24(8): 1683-1695.

In certain embodiments, the sPLA2 inhibitor is chloroquine, hydroxychloroquine, artemotil (arteether), or quinacrine. See Zidovetzki et al. (1993) Inhibition of *Plasmodium falciparum* phospholipase A2 by chloroquine, quinine, and arteether. J Parasitol 79(4):565-570.

In certain embodiments, the sPLA2 inhibitor is 2-(3-(2-amino-2-oxoacetyl)-1-benzyl-2-ethyl-1H-6,7-benzoindol-4-yloxy)acetic acid or derivatives. See Oslund et al. Highly Specific and Broadly Potent Inhibitors of Mammalian Secreted Phospholipases A2, J. Med. Chem. 2008, 51, 4708-4714.

In certain embodiments, this disclosure contemplates that components described herein further contain essential nutrients/micronutrients, protein/carbs and fat for uses as a meal replacement.

In certain embodiments, the composition further comprises an omega 3 fatty acid and/or omega 6 fatty acid. In certain embodiments, the composition further comprises fatty acids. In certain embodiments, the composition comprises medium chain fatty acids with no or low amounts of long chain fatty acids e.g., less than 5% or 2% or 1% of total fatty acids by weight.

In certain embodiments, the composition further comprises a vitamin E (e.g., alpha-tocopherol).

In certain embodiments, the composition further comprises one or more or all of the following: coenzyme Q-10 (ubiquinone), B-vitamins (thiamine, riboflavin, niacin, pyridoxine, cobalamin), alpha lipoic acid, vitamin C (L-ascorbic acid), and vitamin E (alpha-tocopherol).

In certain embodiments, the composition further comprises one or more or all of the following: vitamin K1 (phylloquinone), carnitine, and creatine.

In certain embodiments, the composition further comprises one or more all of the essential amino acids, histidine, isoleucine, leucine, lysine, methionine, phenylalanine, threonine, tryptophan, and valine.

In certain embodiments, the composition further comprises zinc. In certain embodiments, zinc is in amount of greater than 8, 11, 15, 20 mg. In certain embodiments, zinc is in an about of greater than 15, 20, or 30 mg. In certain embodiments, zinc is in an amount of between 30-50 mg.

In certain embodiments, the composition further comprises S-adenosyl-L-methionine (SAMe).

In certain embodiments, the composition further comprises melatonin.

In certain embodiments, the composition further comprises glutathione.

In certain embodiments, the composition further comprises calcium.

In certain embodiments, the composition further comprises magnesium.

In certain embodiments, the composition further comprises selenium.

In certain embodiments, the composition further comprises vitamin A.

In certain embodiments, the composition further comprises vitamin B1.

In certain embodiments, the composition further comprises vitamin B2.

In certain embodiments, the composition further comprises vitamin B3.

In certain embodiments, the composition further comprises vitamin B5.

In certain embodiments, the composition further comprises vitamin B6.

In certain embodiments, the composition further comprises vitamin B7.

In certain embodiments, the composition further comprises vitamin B9.

In certain embodiments, the composition further comprises vitamin B12

In certain embodiments, the composition further comprises vitamin C.

In certain embodiments, the composition further comprises a vitamin D.

In certain embodiments, the composition further comprises a vitamin K.

In certain embodiments, the composition further comprises glutamine.

In certain embodiments, the composition further comprises pyridoxal-5-phosphate.

In certain embodiments, the composition further comprises methylcobalamin.

In certain embodiments, the composition further comprises L-methylfolate (5-MTHF).

In certain embodiments, the composition further comprises citrulline.

In certain embodiments, the composition further comprises citrulline and glycine.

In certain embodiments, the additional components are selected from long or medium chain fatty acids, esters of long chain fatty acids, alpha-lipoic acid, carnitine, an omega-6 fatty acid, esters of omega-6 fatty acid, gamma-linolenic acid, ethyl gamma-linolenate, an omega-9 fatty acid, esters of omega-9 fatty acid, oleic acid, ethyl oleate, zinc, calcium, magnesium, selenium, a vitamin A, a vitamin $B_1$, a vitamin $B_2$, a vitamin $B_3$, a vitamin $B_5$, a vitamin $B_6$, a vitamin $B_7$, a vitamin $B_9$, a vitamin $B_{12}$, vitamin C, vitamin D, vitamin K, S-adenosylmethionine, a phosphocholine, creatine, a coenzyme Q, taurine, tetrahydrobiopterin, methylcobalamin, betaine, pancreatic enzymes, folinic acid, pancrelipase, a leukotriene inhibitor, a arginine, glutamine, N-acetylcysteine, an anti-fungal agent, berberine, an anti-inflammatory agent, anti-bacterial agent, anti-oxidant, saccharides and polysaccharides or combinations thereof.

The compositions and methods of the present disclosure may be utilized to treat an individual in need thereof. In certain embodiments, the individual is a mammal such as a human.

The compositions may contain additional acceptable carrier. The composition can be in dosage unit form such as liquid, tablet, capsule (including sprinkle capsule and gelatin capsule), granule, lyophile for reconstitution, powder, or the like.

An acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose, dextran, antioxidants, such as ascorbic acid or glutathione, chelating agents, low molecular weight proteins or other stabilizers or excipients.

The phrase “carrier” as used herein means a material, composition, or vehicle, such as a liquid or solid filler, diluent, excipient, solvent, or encapsulating material. Each carrier must be “acceptable” in the sense of being compatible with the other ingredients of the formulation and not injurious to the recipient. Some examples of materials which can serve as acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) ethyl alcohol; and (17) other non-toxic compatible substances employed in formulations.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in a non-aqueous liquid, or as pastilles (using an inert base, such as gelatin and glycerin, or sucrose and acacia) and the like, each containing a predetermined amount of compounds. Compositions or compounds may also be administered as a bolus, electuary, or paste.

To prepare solid dosage forms for oral administration (capsules (including sprinkle capsules and gelatin capsules), tablets, pills, powders, granules and the like), the active ingredient is mixed with one or more acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the compositions, such as dragees, capsules (including sprinkle capsules and gelatin capsules), pills and granules, may optionally be scored or prepared with coatings and shells, such as enteric coatings and other coatings. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Compositions suitable for parenteral administration may comprise one or more active compounds in combination with one or more sterile isotonic solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable nonaqueous carriers that may be employed in the compositions of the disclosure include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable form may be brought about by the inclusion of agents that delay absorption such as aluminum monostearate and gelatin.

If desired, the effective daily dose of the compounds may be administered as one, two, three, four, five, six or more sub-doses administered separately at appropriate intervals throughout the day, optionally, in unit dosage forms. In certain embodiments of the present disclosure, the compounds may be administered two or three times daily. In preferred embodiments, the compounds will be administered once daily.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Low Arginine Bioavailability in Patients with SARS-CoV-2 Infection

Low plasma arginine bioavailability has been implicated in endothelial dysfunction and immune dysregulation. The role of arginine in COVID-19 could contribute to cellular damage if low. Experiments were performed to determine whether arginine bioavailability in adults and children with COVID-19 vs healthy controls. It is possible that arginine bioavailability would be low in patients with COVID-19 and multisystem inflammatory syndrome in children (MIS-C).

A prospective observational study of three patient cohorts was conducted; arginine bioavailability was determined in asymptomatic healthy controls, adults hospitalized with COVID-19, and hospitalized children/adolescents $<21$ years old with COVID-19, MIS-C, or asymptomatic SARS-CoV-2 infection identified on admission screen. Mean patient plasma amino acids were compared to controls. Arginine-to-ornithine ratio, a biomarker of arginase activity, and global arginine bioavailability ratio (GABR, arginine/(ornithine+citrulline) were assessed in all three groups.

A total of 80 patients were included (28 controls, 32 adults with COVID-19, and 20 pediatric patients with COVID-19/MIS-C). Mean plasma arginine and arginine bioavailability ratios were lower among adult and pediatric patients with COVID-19/MIS-C compared to controls. There was no difference between arginine bioavailability in children with COVID-19 vs MIS-C. Adults and children with COVID-19 and MIS-C in our cohort had low arginine bioavailability compared to healthy adult controls. This may contribute to immune dysregulation and endothelial dysfunction in COVID-19. Low arginine-to-ornithine ratio in patients with COVID-19 or MIS-C suggests an elevation of arginase activity.

Endothelial dysfunction may play a role in the development of lung injury in COVID-19 in both adults and children. Low bioavailability of the amino acid arginine has been implicated in the development of endothelial dysfunction as well as T-cell dysregulation and contributes to the pathophysiology of multiple diseases. Amino acids in hospitalized adults and children with COVID-19 were evaluated for the possibility that arginine bioavailability would be low compared to healthy controls.

A total of 80 participants were included (28 adult controls, 32 hospitalized adults with COVID-19, and 20 hospitalized children/adolescents). Patient characteristics are summarized in the table of FIG. 4. Within the pediatric cohort, nine had COVID-19, nine had MIS-C, and two were asymptomatic.

The amino acid profiles in COVID-19 patients were abnormal (see table in FIG. 5). Mean plasma arginine bioavailability among controls who were seronegative for SARS-CoV-2 IgG antibodies was similar to values among controls who had anti-SARS-CoV-2 IgG antibodies ($96.8\pm30.0$ vs $87.8\pm28.6$ μmol/L, respectively, $p=0.43$).

Figure 2:
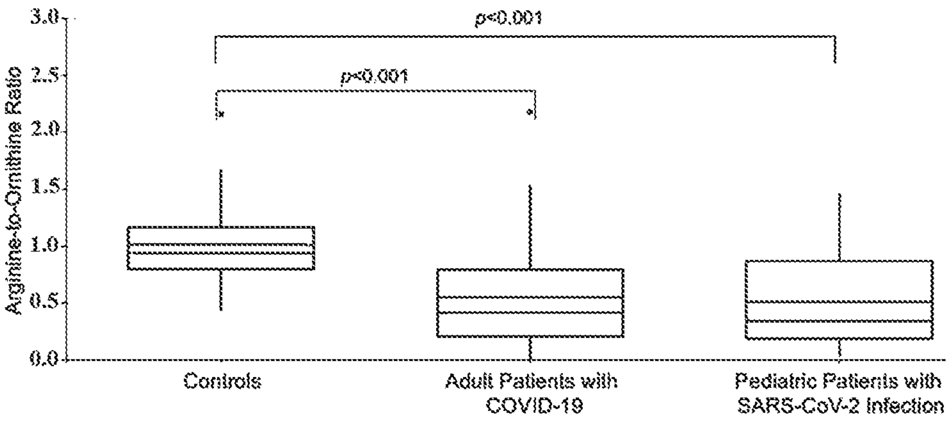
FIG. 2 shows data on arginine-to-ornithine ratios among the three cohorts.
Figure 3:
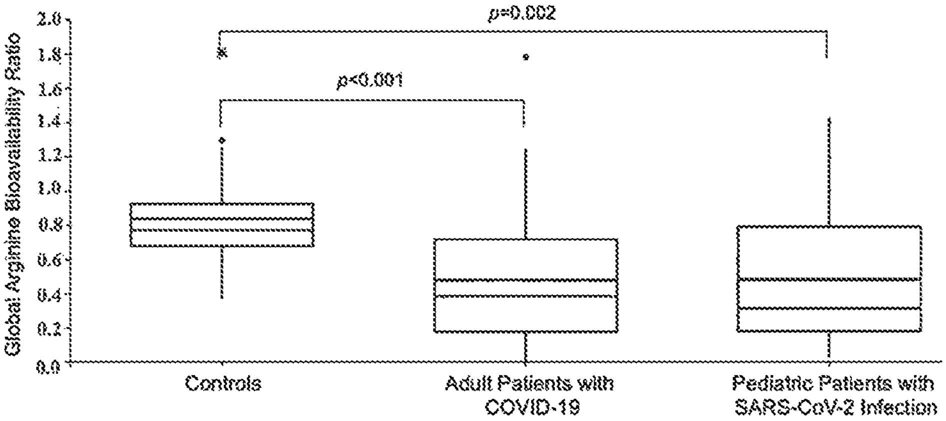
FIG. 3 shows data on global arginine bioavailability ratios among the three cohorts.

Arginine concentration less than 50 μmol/L was identified in 53.1% (17/32) adults and 66.7% (12/20) of children with SARS-CoV-2 infection, but in only 3.6% (1/28) of controls. Arginine bioavailability, measured by arginine-to-ornithine ratio and GABR, was significantly lower among both adults and children with SARS-CoV-2 infection compared to controls (see FIGS. 1-3). Arginine bioavailability among children with MIS-C was also significantly lower than controls ($p<0.001$) but did not differ significantly from adults or children with COVID-19 ($p=0.35$). There was no correlation between plasma arginine concentration and lymphocyte count among children with SARS-CoV-2 infection ($r=0.23$, $p=0.35$), but a trend with arginine-to-ornithine ($r=0.44$, $p=0.07$), and GABR ($r=0.43$, $p=0.07$) suggestive of a link to immune function.

Some propose arginine depletion and the use of arginase reducing therapies as potential treatments for COVID-19. See Grimes, et al. Arginine Depletion as a Therapeutic Approach for Patients with COVID-19. Int J Infect Dis. 102, 566-570 (2020). However, data reported herein indicates this may potentially exacerbate COVID-19 illness given the extant arginine depletion in COVID-19. Finding reported herein indicate acute arginine depletion in COVID-19 among adults is consistent with findings from a recent study of 26 severely ill adults in France. See Reizine, et al. SARS-CoV-2-Induced ARDS Associates with MDSC Expansion, Lymphocyte Dysfunction, and Arginine Shortage. J Clin Immunol, 1-11 (2021). Unique is the identification of arginine depletion in both children with SARS-CoV-2 infection and MIS-C. It is believed that arginine depletion in COVID-19 and MIS-C may contribute to endothelial dysfunction, T-cell dysregulation, and coagulopathy that have been observed in COVID-19.

Low arginine-to-ornithine and GABR suggest increased arginase activity and potentially impaired arginine synthesis, respectively, in COVID-19 and MIS-C. Furthermore, as adult controls with anti-SARS-CoV-2 antibodies who recovered from COVID-19 had normal arginine bioavailability, arginine depletion during COVID-19 appears to be transient. Although there was no correlation between arginine concentration and lymphocyte counts, a trend with arginine bioavailability ratios was observed. Ultimately, a majority of COVID-19 patients had low arginine levels, which has been implicated in T-cell dysfunction. T cells stimulated in arginine concentrations less than 50 μmol/L causes a decreased expression of the CD3ζ chain, the primary signaling chain in the T cell receptor complex, impairing T cell proliferation and IFN-γ production.

Multiple amino acid anomalies were noted in patients with COVID-19 beyond arginine that may provide insight to metabolic derangements and could have clinical consequences. Compared to controls, glutamine, an arginine precursor that becomes important during critical illness, was significantly lower in adult patients with COVID-19 but not among the pediatric cohort. Tryptophan, a serotonin precursor was reduced by nearly 50% in COVID-19 patients, which may have neuropsychiatric implications. Phenylalanine was high while citrulline was low in COVID-19 patients, implicating potential dysfunction of tetrahydrobiopterin, an essential nitric oxide synthase co-factor. Decreased energy metabolism, through both the TCA cycle and the citric acid cycle, are suggested by COVID-19 amino acid profiles. These data confirm metabolic derangements identified in adults with SARS-CoV-2 infection may also affect children with COVID-19 and MIS-C.

Arginine/BH4/Arginase Inhibitor in Combination that Targets the Arginine-Nitric Oxide Pathway A dietary/nutritional formulation of arginine, BH4, and arginase inhibitor in combination with additional ingredients are contemplated to make a robust COVID treatment formula which also includes 5HTP will impact serotonin. One cannot convert tryptophan to serotonin if BH4 is low/dysfunctional that could result in neuropsychic symptoms. Vijay et al. report a critical role of phospholipase A2 group IID (sPLA2) in age-related susceptibility to severe acute respiratory syndrome-CoV infection. J Exp Med, 2015, 212(11):1851-1868. Also contemplated in the formulation is the inclusion of a sPLA2 inhibitor such as annexin V and diannexin (a recombinant form of the endogenous human annexin V protein). See Neidlinger et al. Secretory phospholipase A2 attacks erythrocytes with externalized phosphatidylserine, Journal of Surgical Research, 2004, 121(2):277. Other contemplated PLA2 inhibitors are varespladib, varespladib methyl ester, varespladib ethyl ester, and darapladib. Also contemplated are the addition of mitochondrial cocktail of ingredients such as an omega 3 fatty acid, a vitamin E, other essential amino acids, SAMe, melatonin, and GSH.

The above formulation may also be delivered via IV as an intravenous total parenteral nutrition (TPN) for COVID. Patients are on ventilators for weeks. There is a need for COVID TPN that is higher in arginine, and including BH4 etc.

A formulation of arginine, BH4, and arginase inhibitor in combination with additional ingredients are contemplated. Additional ingredients may be a formula which also includes essential amino acid and 5HTP will impact serotonin.

Additional ingredients may be a formula which also includes long or medium chain fatty acids, poly unsaturated fatty acids (DHA/EPA etc), higher dose of vitamin E to maximize neurological development & function that is compromised in conditions of malabsorption/SIBO, and additional ingredients to aid digestion (pancreatic enzymes), address an abnormal gut microbiome (probiotics, berberine), and address inflammation and/or oxidative stress (curcumin, sulforaphane, etc).

This formulation typically contains essential vitamins, micronutrients, amino acids and fats such as monosaccharides (glucose), medium chain triglycerides (from coconut and/or palm kernel oil), soybean oil, calcium glycerophosphate, magnesium gluconate L-glutamine, L-lysine acetate, L-leucine, L-arginine acetate, potassium chloride, L-valine, citric acid, L-isoleucine, L-aspartic acid, L-alanine, L-phenylalanine, L-serine, L-proline, L-threonine, sodium citrate, L-tyrosine, L-glutamic acid, potassium citrate, glycine, L-histidine hydrochloride, L-methionine, choline bitartrate, L-cystine, polyglycerol esters of fatty acids, L-tryptophan, sodium phosphate, ascorbic acid, potassium sorbate and BHA/BHT (to Maintain Freshness), M-inositol, taurine, alpha-tocopherol acetate, ferrous sulfate, L-carnitine, zinc sulfate, niacinamide, calcium pantothenate, vitamin D3, copper gluconate, vitamin A palmitate, manganese sulfate, pyridoxine hydrochloride, thiamine hydrochloride, riboflavin, beta carotene, chromium chloride, sodium molybdate, folic acid, potassium iodide, biotin, sodium selenite, phytonadione, vitamin B12.

COVID Cocktail

In addition to arginine, components such as tetrahydrobiopterin (BH4) are considered important to add to a dietary formula for someone infected or recovering from a coronavirus infection. The unique pattern of abnormality (high phenylalanine and low citrulline) implicates abnormal BH4 function. An example formulation are contemplated to include: arginine (up to 10 grams per dose; 30 grams per day); BH4; glutamine; 5HTP; citrulline, glycine, additional amino acids, L-carnitine or L-acetyl-carnitine, creatine monohydrate, SAMe (S-adenosylmethionine).

sPLA2 is a biomarker of severe inflammation. Preliminary analysis demonstrated high levels of sPLA2 in acute COVID-19 and some MIS-C samples. Other contemplated ingredients (optional) are an arginase inhibitor, an sPL2 inhibitor, vitamin D, glutathione or GSH precursors, zinc, vitamin C, vitamin E/omega 3 (decrease clotting), melatonin, and a mitochondrial cocktail. Examples of ingredients in a mitochondrial cocktail include active B-vitamins (including methylcobalamin, L-methylfolate (5-MTHF), B1 (thiamine), B2 (riboflavin), niacin, B6 (5-P-5), biotin, pantothenic acid, alpha lipoic acid, Co-Q10, and phosphatidylcholine.

What is claimed is:

1. A composition comprising arginine, tetrahydrobiopterin, 5-hydroxytryptophan and an arginase inhibitor.

2. The composition of claim 1, further comprising sPLA2 inhibitor.

3. The composition of claim 2, wherein the sPLA2 inhibitor is diannexin or annexin V.

4. The composition of claim 3, further comprising an omega 3 fatty acid and/or omega 6 fatty acid.

5. The composition of claim 4, further comprising alpha-tocopherol.

6. The composition of claim 1, further comprising one or more or all of the following: ubiquinone thiamine, riboflavin, niacin, pyridoxine, cobalamin, alpha lipoic acid, L-ascorbic acid and alpha-tocopherol.

7. The composition of claim 6, further comprising one or more or all of the following: a vitamin K1 (phylloquinone), L-carnitine, and creatine.

8. The composition of claim 7, further comprising one or more essential amino acids.

9. The composition of claim 8, further comprising S-adenosyl-L-methionine (SAMe).

10. The composition of claim 9, further comprising melatonin.

11. The composition of claim 10, further comprising glutathione.

12. A method of treating or preventing acute respiratory syndrome comprising administering a composition comprising arginine, tetrahydrobiopterin, and an arginase inhibitor to a subject in need thereof.

13. The method of claim 12, wherein the subject is diagnosed with a SARS-COV-2 infection.

14. The method of claim 12, wherein the composition is administered daily.

15. The method of claim 14, wherein the composition is administered daily for more than 3, 5, 7 days or two weeks.

16. The method of claim 12, wherein the subject is diagnosed with multisystem inflammatory syndrome in children (MIS-C) and in adults (MIS-A).

17. The method of claim 16, wherein the subject is less than 25, 20, 15, or 10 years old.

18. The method of claim 12, wherein the subject is diagnosed with fatigue, shortness of breath, brain fog, joint pain, chest pain, and optionally diabetes, stroke, heart rhythm abnormality, and/or blood clot in the lungs.

19. The method of claim 12, wherein the subject is more than 65 or 75 years old and/or diagnosed with a severe acute infection requiring intensive care, pre-existing respiratory illness, obesity, diabetes, high blood pressure, chronic cardiovascular disease, chronic kidney disease, organ transplant, or active cancer.

* * * * *